(12) United States Patent
Herwig et al.

(10) Patent No.: US 7,608,738 B2
(45) Date of Patent: Oct. 27, 2009

(54) COAMMOXIDATION OF KETONES

(75) Inventors: Juergen Herwig, Huenxe (DE); Martin Roos, Haltern am See (DE); Georg Oenbrink, Duelmen (DE); Bernd Guenzel, Haltern am See (DE); Dirk Kuppert, Recklinghausen (DE)

(73) Assignee: Degussa AG, Duesseldorf (DE)

( * ) Notice: Subject to any disclaimer, the term of this patent is extended or adjusted under 35 U.S.C. 154(b) by 255 days.

(21) Appl. No.: 10/572,594

(22) PCT Filed: Aug. 2, 2004

(86) PCT No.: PCT/EP2004/051684

§ 371 (c)(1),
(2), (4) Date: Apr. 2, 2007

(87) PCT Pub. No.: WO2005/063691

PCT Pub. Date: Jul. 14, 2005

(65) Prior Publication Data

US 2008/0249300 A1    Oct. 9, 2008

(30) Foreign Application Priority Data

Sep. 25, 2003    (DE) .............................. 103 44 469

(51) Int. Cl.
*C07C 251/32* (2006.01)
*C07C 249/04* (2006.01)
(52) U.S. Cl. .................. 564/253; 564/265; 564/267
(58) Field of Classification Search .................. 564/253, 564/265, 267
See application file for complete search history.

(56) References Cited

U.S. PATENT DOCUMENTS

| | | | |
|---|---|---|---|
| 5,498,793 A | 3/1996 | Mantegazza et al. | |
| 6,403,851 B1 | 6/2002 | Wilczok et al. | |
| 6,407,304 B2 | 6/2002 | Schiffer et al. | |
| 6,444,855 B1 | 9/2002 | Esser et al. | |
| 6,462,235 B1 | 10/2002 | Thiele et al. | |
| 6,610,864 B2 | 8/2003 | Krebs et al. | |
| 6,613,946 B2 | 9/2003 | Grund et al. | |
| 6,620,970 B2 | 9/2003 | Schiffer et al. | |
| 6,639,108 B2 | 10/2003 | Schiffer et al. | |
| 6,664,423 B2 | 12/2003 | Herwig et al. | |
| 6,828,449 B2 | 12/2004 | Herwig et al. | |
| 6,861,540 B2 | 3/2005 | Herwig et al. | |
| 6,926,809 B2 | 8/2005 | Puschner et al. | |
| 6,927,308 B2 | 8/2005 | Leininger et al. | |
| 2002/0030014 A1* | 3/2002 | Leconte ...................... 210/634 | |
| 2003/0100795 A1 | 5/2003 | Herwig et al. | |
| 2003/0105356 A1 | 6/2003 | Schiffer et al. | |
| 2003/0195374 A1 | 10/2003 | Herwig et al. | |
| 2004/0225168 A1 | 11/2004 | Herwig et al. | |

OTHER PUBLICATIONS

U.S. Appl. No. 11/688,505, filed Mar. 20, 2007, Herwig et al.
U.S. Appl. No. 11/719,164, filed May 11, 2007, Kuppert et al.
U.S. Appl. No. 12/296,498, filed Oct. 8, 2008, Roos et al.
U.S. Appl. No. 12/207,169, filed Sep. 9, 2008, Baumgarten et al.

* cited by examiner

*Primary Examiner*—Sikarl A Witherspoon
(74) *Attorney, Agent, or Firm*—Oblon, Spivak, McClelland, Maier & Neustadt, L.L.P.

(57) ABSTRACT

The present invention relates to a process for the coammoximation, that is to say for the simultaneous ammoximation, of ketones, in particular of cyclic ketones such as cyclododecanone and cyclohexanone. Ammoximation is taken to mean here the preparation of oximes from ketones or aldehydes together with hydrogen peroxide and ammonia and in the presence of a catalyst which essentially consists of silicon, titanium and oxygen, for example titanium silicalite.

22 Claims, No Drawings

COAMMOXIDATION OF KETONES

The present invention relates to a process for the coammoximation, that is to say for the simultaneous ammoximation, of ketones, in particular of cyclic ketones such as cyclododecanone and cyclohexanone. Ammoximation is taken to mean here the preparation of oximes from ketones or aldehydes together with hydrogen peroxide and ammonia and in the presence of a catalyst which essentially consists of silicon, titanium and oxygen, for example titanium silicalite.

The ammoximation of carbonyl compounds has frequently been described in the literature. For instance EP 0 208 311 describes a process for preparing cyclohexanone oxime from cyclohexanone, ammonia, hydrogen peroxide and a titanium silicalite as catalyst. In this publication, only cyclohexanone is used as carbonyl compound.

EP 0 496 385 describes a multistage process for preparing oximes from carbonyl compounds by ammoximation in liquid phase. Although various carbonyl compounds, for example cyclohexanone, acetophenone or cyclododecanone, are used individually, there is no indication given of the use of mixtures of carbonyl compounds.

EP 0 564 040 describes a two-stage process for the ammoximation of carbonyl compounds in liquid phase. However, here also, only the ammoximation of one carbonyl compound is claimed, no indication is given of any possible mixtures of carbonyl compounds.

Finally, DE-A 2 111 792 describes a process for preparing a cyclohexanone oxime/cyclododecanone oxime mixture. Here, the oxime is formed not by ammoximation, but by classical oxime formation by reacting the ketones with hydroxylamine in the form of the hydroxylamine sulfate. The oximation process is carried out in two stages, the first reaction stage being performed at a pH of 3-4.5 and at 80-90° C. and the second reaction stage at a pH of 5-6 and at 90-110° C. This two-stage procedure is described as advantageous for minimizing hydroxylamine decomposition by iron ions which, under different conditions, would lead to high losses of the relatively expensive hydroxylamine starting material. Disadvantages of this process are, inter alia, the use of the relatively expensive hydroxylamine sulfate and the complex procedure in two stages, and also the exact maintenance of pH conditions with accompanying increased chemical consumption in the form of base to be continuously fed, for example ammonia for the neutralization (example). Likewise disadvantageous is the inescapable production of sulfate salt, due to the use of hydroxylamine sulfate, which salt must be disposed of in a complex manner.

The known ammoximation processes, starting from simple fundamental materials ammonia and hydrogen peroxide, relate solely to the use of individual carbonyl components which are prepared by a process which is individually optimized for each component.

However, in the literature, nowhere is there a description of the preparation of a mixture of various ketone oximes such as cyclododecanone oxime and cyclohexanone oxime by an up-to-date ammoximation process directly, starting from the simple fundamental materials ammonia and hydrogen peroxide.

However, such a process would have the advantage that, for the quantitatively smaller product, here, for example, cyclododecanone oxime, use could be made of the scaling effect of the quantitatively greater product cyclohexanone oxime, that is to say without relatively large additional capital expenditure, for example in addition to cyclohexanone oxime, cyclododecanone oxime could be produced simultaneously in an existing caprolactam plant.

The object was therefore to find a process which makes possible the ammoximation of mixtures of ketones, particularly the industrially important ketones cyclohexanone and cyclododecanone (CDON), by an up-to-date ammoximation process directly starting from the simple fundamental materials ammonia and hydrogen peroxide and a suitable catalyst, and which avoids the disadvantages of the previously known processes.

This object, and also other objects which are not mentioned explicitly, but which can be simply derived or concluded from the facts discussed herein, are achieved by a process as claimed in claim 1. Expedient forms and modifications of the inventive process are claimed in the subclaims referred back to claim 1.

The fact that, for the coammoximation of at least two ketones, a process is used in which a mixture of at least one cyclic ketone and at least one further ketone is reacted with ammonia, hydrogen peroxide, a catalyst which essentially consists of silicon, titanium and oxygen, in the presence of a solvent in one step to give a corresponding mixture of ketone oximes makes it possible to overcome the disadvantages of the prior art which are described in more detail above.

The catalyst preferably used is titanium silicalite.

For the inventive process, use can be made of a mixture of at least two ketones, for example a mixture of one cyclic ketone and one non-cyclic ketone. For example, mixtures of acetone and cyclododecanone, or acetophenone and cyclododecanone, or else mixtures of other ketones which can act as substrates for the ammoximation can be used.

Preferably, however, use is made of a mixture of two or more cyclic ketones selected from the group consisting of cyclic ketones having 5 to 20 carbon atoms, in particular selected from the group consisting of cyclic ketones having 6 to 12 carbon atoms, for example cyclohexanone and cyclooctanone.

According to the invention, extraordinary preference is given, however, to using a mixture of cyclohexanone and cyclododecanone. In this case, preferably, use is made of mixtures of cyclohexanone and cyclododecanone in a ratio of 10:1 to 1:10 parts by volume, in particular of 5:1 to 1:5 parts by volume.

The present invention therefore relates to a process for producing mixtures of oximes, preferably cyclic oximes, in particular mixtures of cyclododecanone oxime and cyclohexanone oxime, from the corresponding ketones, together with hydrogen peroxide and ammonia in the presence of a catalyst system, the catalyst system preferably consisting of at least two components, such that one component is made up on a basis of titanium, silicon and oxygen, preferably in the form of a titanium silicalite, and optionally an additional component consists of at least one ammonium salt as cocatalyst.

In addition, in the system, there can be further present at least one solvent or at least one interphase contactor, for example one or more surfactants.

The titanium-, silicon- and oxygen-containing catalyst can be used as a solid, not only crystalline as powder, but also as a shaped body. If the catalyst is used as shaped body, other components, in particular neutral or acidic inorganic or organic solids, can be present, such as aluminum oxide or silicon oxide, which act as binder in the shaped body. The catalyst can be used in a manner familiar to those skilled in the art in a batch reaction system or in a continuous reaction system, for example a continuous-flow fixed-bed reactor, and the coammoximation can be carried out accordingly batchwise or continuously.

As homogeneous cocatalyst for the inventive process, use can be made of all ammonium salts which are sufficiently soluble in the reaction mixture and whose anions do not have a disadvantageous effect on the course of the reaction. Non-limiting examples are ammonium salts of strong mineral acids, for example ammonium chloride, ammonium sulfate, ammonium silicate or ammonium nitrate, and also ammonium salts of monobasic or polybasic carboxylic acids, for example ammonium formate, ammonium acetate, ammonium propionate, ammonium citrate or ammonium benzoate. The amount of ammonium salt can be chosen within broad limits. Preferably, the ammonium salt is used at a concentration of 0.001 mol/kg to 1 mol/kg in the reaction mixture. The ammonium salt is preferably added either directly to the reaction mixture or to the hydrogen peroxide used in the reaction.

In a further embodiment of the invention, the ammonium salt used as cocatalyst is generated in the reaction mixture from a Brönsted acid and the ammonia used for the reaction. Non-limiting examples of suitable Brönsted acids are mineral acids, for example hydrochloric acid, sulfuric acid, salicic acid and nitric acid, and monobasic or polybasic carboxylic acids, for example formic acid, acetic acid, propionic acid, oxalic acid, glutaric acid, citric acid or benzoic acid. The Brönsted acid is preferably either added directly to the reaction mixture or to the hydrogen peroxide used for the reaction. The cocatalyst remains in the aqueous phase after the reaction.

As solvents, use can be made of at least partially water-miscible solvents, such as aliphatic alcohols, for example ethanol, propanol, 1-butanol, 2-butanol, isobutanol, tert-butanol, in pure form or as mixtures. In this case a liquid phase then forms. In addition, use can be made of water-immiscible solvents, for example aromatics, such as toluene, or $C_6$-$C_{12}$-alicyclic hydrocarbons, and in this case two liquid phases then form. Preference is given to water-miscible solvents cyclooctane, cyclododecane and hexahydrocumene or mixtures thereof. The advantage of the last-mentioned solvents is that they are resistant to sulfuric acid.

To accelerate the reaction, in particular when water-immiscible solvents are used, use can be made of interphase contactors.

As interphase contactors, use can be made of all surfactants and phase-transfer catalysts provided that they are stable, that is to say are not oxidized in situ. Examples of such interphase contactors are alkanesulfonates, for example Marlon PS 30 from Sasol. Other possible interphase contactors are quaternary ammonium salts of the type $[NR^1R^2R^3R^4]^+X^-$, in which the radicals $R^1$-$R^4$ independently of one another can be aliphatic hydrocarbon radicals of $C_1$-$C_{20}$ and $X^-$ is an anion, for example chloride, bromide, iodide, hydrogen sulfate.

For example, here, advantageously use can be made of tetrabutylammonium bromide, tetrabutylammonium chloride, tetraethylammonium bromide, tetraethylammonium chloride, benzyltriethylammonium chloride, benzyltrimethylammonium chloride, methyltributyl-ammonium chloride or methyltricaprylammonium chloride.

As interphase contactors, preferably, use is made of alkanesulfonates and/or quaternary ammonium salts at a concentration of 0.01-5% by weight, based on the total reaction mixture.

Hydrogen peroxide is used as aqueous solution at commercially conventional concentrations, preferably in the range from 10% to 70%, in particular at least 30% strength. Ammonia is fed to the reactor either as concentrated aqueous solution (at least 20% strength), or preferably as pure ammonia in gaseous or condensed form. Advantages result in the addition of gaseous or condensed ammonia and in the case of highly concentrated peroxide solutions from the smaller amount of introduced water which needs to be separated off during the workup of the reaction mixture.

The reaction temperature of the ammoximation is in the range from 20 to 150° C., preferably in the range from 50 to 120° C., and particularly preferably in the range from 60 to 100° C. The reaction is carried out either at atmospheric pressure, that is to say the vapor pressure of the respective solvent at the reaction temperature, or at a superatmospheric pressure, preferably between 1 and 10 bar. The superatmospheric pressure can be set using ammonia or an inert gas. If the reactor is closed, the pressure increases due to the formation of gaseous decomposition products in side reactions (especially nitrogen and oxygen) during the reaction. It is advantageous to run the reactor isobarically, by allowing gaseous decomposition products to escape in a controlled manner via a gentle offgas stream, for example using a bubble counter on a laboratory scale or an industrial pressure regulator, and if appropriate consumed ammonia being replenished.

During the ammoximation reaction, carbonyl compounds and hydrogen peroxide can in each case be added batchwise or continuously. Since $H_2O_2$ decomposition reactions always occur from time to time, complete ketone conversion requires an excess of peroxide solution, which excess can be minimized by a suitable reaction procedure and the inventive catalyst systems. In the experiments it has proved to be advantageous either to introduce the carbonyl compound at the start of the reaction or to add it in equimolar amounts in parallel to the hydrogen peroxide and to replenish the required excess of peroxide according to consumption after carbonyl addition has been completed.

The mixtures of various ketone oximes prepared in this manner can then be separated into their individual components in a known manner, for example crystallization or optionally distillation. However, it is equally possible to feed the mixtures to a subsequent reaction stage and to separate the product mixtures then produced there using said separation methods.

In particular, it is of great advantage to convert the inventively obtained mixtures of cyclic ketone oximes by Beckmann rearrangement in the corresponding lactam mixtures and then to separate the resultant lactams.

Here, preference is given especially to producing mixtures of lactams which are selected from the group consisting of caprolactam, enantholactam, caprylolactam, pelargonolactam, decanolactam, undecanolactam and laurolactam, but in particular producing mixtures of caprolactam and laurolactam, since these products are frequently used for the industrial preparation of corresponding polyamides.

EXAMPLE 450 g of a solution containing 12.5% by weight of cyclohexanone (574 mmol) and 12.5% weight of cyclododecanone (309 mmol), 241 g of 25% strength ammonia solution (3.5 mol), 0.39 g of Marlon PS30 and 7 g of ammonium acetate were charged into a 1.5 l glass reactor. The solution was pumped at a speed of 300 m/min through an external fixed bed which contains 100 g of a catalyst consisting of 80% titanium silicalite (TS1) and 20% aluminum oxide.

The mixture was heated to 85° C. and then, over the course of 8 h, 90 g of 50% strength hydrogen peroxide solution (1.32 mol) were added by pumping. After this time, the conversion rate of cyclohexanone to cyclohexanone oxime was complete and the conversion of cyclododecanone to cyclododecanone oxime was 96.5%.

The invention claimed is:

1. A process for the coammoximation of at least two different ketones present in a volume ratio of 10:1 to 1:10, which comprises
reacting a mixture of at least one cyclic ketone and at least one further ketone with ammonia and hydrogen peroxide in the presence of a solid catalyst which consists essentially of silicon, titanium and oxygen, and a solvent;
wherein the reacting is carried out in one step to give a corresponding mixture of ketone oximes by simultaneously ammoximating the different ketones.

2. The process as claimed in claim 1, wherein at least one ammonium salt is present as a cocatalyst during the reacting.

3. The process as claimed in claim 1, wherein the ketones of the mixture are cyclic ketones having 5 to 20 carbon atoms.

4. The process as claimed in claim 3, wherein the cyclic ketones have 6 to 12 carbon atoms.

5. The process as claimed in claim 4, wherein the cyclic ketones are cyclohexanone and cyclododecanone.

6. The process as claimed in claim 1, wherein the reacting is carried out with ammonia having a concentration of at least 20% in water or pure ammonia.

7. The process as claimed in claim 1, wherein the aqueous hydrogen peroxide has at a concentration of 10-70%.

8. The process as claimed in claim 1, wherein the solid catalyst is titanium silicalite.

9. The process as claimed in claim 1, wherein a cocatalyst comprising an ammonium salt of at least one of a mineral acid and a carboxylic acid is present during the reacting.

10. The process as claimed in claim 2, wherein the cocatalyst is generated in the reaction mixture in situ from a Brönsted acid and ammonia.

11. The process as claimed in claim 2, wherein the at least one ammonium salt is present in the reaction mixture at a concentration of 0.001 to 1 mol/kg.

12. The process as claimed in claim 1, wherein an at least partially water-miscible solvent, or a water-immiscible solvent is present during the reacting.

13. The process as claimed in claim 1, wherein a water-immiscible solvent comprising an interphase contactor is present during the reacting.

14. The process as claimed in claim 13, wherein, the interphase contactor comprises at least one of alkanesulfonates and quaternary ammonium salts present at a concentration of 0.01 to 5% by weight, based on the total reaction mixture.

15. The process as claimed in claim 1, wherein the reaction temperature is in the range from 20 to 150° C.

16. The process as claimed in claim 15, wherein the reaction temperature is in the range from 50 to 120° C.

17. The process as claimed in claim 1, wherein the ammoximating is carried out in a continuous or in a batchwise reaction system.

18. The process as claimed in claim 1, wherein the reaction is carried out at a pressure of 1 to 10 bar.

19. A method for preparing lactams by Beckmann rearrangement comprising utilizing the mixture of ketone oximes prepared by the process as claimed in claim 1.

20. The method as claimed in claim 19, wherein the lactams prepared are at least one selected from the group consisting of caprolactam, enantholactam, caprylolactam, pelargonolactam, decanolactam, undecanolactam and laurolactam.

21. The process as claimed in claim 1, wherein the ammoximating is performed in the presence of a solvent in the one step to give a corresponding mixture of ketone oximes.

22. The process as claimed in claim 1, wherein the two different ketones are present in a volume ratio of 5:1 to 1:5.

* * * * *